United States Patent
Chung et al.

(10) Patent No.: US 9,429,779 B2
(45) Date of Patent: Aug. 30, 2016

(54) ELECTRO-OPTIC MODULATOR INCLUDING COMPOSITE MATERIALS AND TESTING APPARATUS INCLUDING THE SAME

(71) Applicants: Samsung Electronics Co., Ltd., Suwon-si, Gyeonggi-do (KR); Samsung Display Co., Ltd., Yongin-si, Gyeonggi-do (KR)

(72) Inventors: Chi-youn Chung, Seoul (KR); Heung-mo Koo, Suwon-si (KR); Hye-won Kim, Seoul (KR); Myoung-ki Ahn, Yongin-si (KR); Il-hyoung Lee, Daejeon (KR); Jung-sub Lee, Hwaseong-si (KR); Sung-mo Gu, Daegu (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/802,194

(22) Filed: Jul. 17, 2015

(65) Prior Publication Data

US 2016/0054600 A1    Feb. 25, 2016

(30) Foreign Application Priority Data

Aug. 19, 2014  (KR) .................. 10-2014-0107764

(51) Int. Cl.
| | |
|---|---|
| *G01J 4/00* | (2006.01) |
| *G02F 1/13* | (2006.01) |
| *G02F 1/1334* | (2006.01) |
| *G01N 21/958* | (2006.01) |
| *G02F 1/137* | (2006.01) |

(52) U.S. Cl.
CPC ........... *G02F 1/1309* (2013.01); *G01N 21/958* (2013.01); *G02F 1/1334* (2013.01); *G02F 1/13718* (2013.01)

(58) Field of Classification Search
CPC .. G02F 1/37; G02F 1/1309; G02F 1/133553; G02F 1/13439; G01N 21/211; G01N 21/21; G01N 2021/213; G01J 4/00; G01B 11/0641
USPC .................................................. 356/300–445
See application file for complete search history.

(56) References Cited

U.S. PATENT DOCUMENTS

| | | | |
|---|---|---|---|
| 6,266,113 B1 * | 7/2001 | Yamazaki | ......... G02F 1/133533 349/105 |
| 6,266,133 B1 | 7/2001 | Miyajima et al. | |
| 6,628,439 B2 | 9/2003 | Shiozawa et al. | |
| 7,006,669 B1 | 2/2006 | Lavagnino et al. | |
| 7,428,057 B2 | 9/2008 | De Lega et al. | |
| 7,446,882 B2 | 11/2008 | De Lega et al. | |
| 7,616,323 B2 | 11/2009 | De Lega et al. | |
| 7,952,724 B2 | 5/2011 | De Lega et al. | |

(Continued)

FOREIGN PATENT DOCUMENTS

| | | |
|---|---|---|
| JP | 2003-187222 | 7/2003 |
| JP | 2004-279365 | 10/2004 |

(Continued)

*Primary Examiner* — Abdullahi Nur
(74) *Attorney, Agent, or Firm* — Myers Bigel & Sibley

(57) ABSTRACT

An electro-optic modulator can include a polymer film including liquid crystal (LC) droplets in the polymer film and a transparent electrode layer on an upper surface of the polymer film. A cholesteric liquid crystal (CLC) polymer reflection film can be on a lower surface of the polymer film opposite the transparent electrode layer.

18 Claims, 9 Drawing Sheets

(56) References Cited

U.S. PATENT DOCUMENTS

| | | |
|---|---|---|
| 8,378,708 B2 | 2/2013 | Jun et al. |
| 2006/0187384 A1 | 8/2006 | Hisatake |
| 2006/0250545 A1* | 11/2006 | Hsieh ............... G02F 1/1334 349/86 |
| 2007/0263226 A1* | 11/2007 | Kurtz ............... A61B 5/0059 356/492 |
| 2008/0088849 A1* | 4/2008 | De Lega ........... G01B 9/02044 356/450 |
| 2008/0192157 A1 | 8/2008 | Gan et al. |
| 2009/0059067 A1 | 3/2009 | Takanohashi et al. |
| 2010/0194414 A1 | 8/2010 | Jun et al. |
| 2012/0287377 A1 | 11/2012 | Kim et al. |

FOREIGN PATENT DOCUMENTS

| | | |
|---|---|---|
| JP | 2007-114629 | 5/2007 |
| JP | 2000-036582 | 2/2009 |
| JP | 2013-250188 | 12/2013 |
| KR | 20070104615 | 10/2007 |
| KR | 100778170 | 11/2007 |
| KR | 20080062880 | 7/2008 |
| KR | 100902349 | 6/2009 |
| KR | 10-2010-0126015 A | 12/2010 |
| KR | 10-2011-0051027 A | 5/2011 |
| KR | 20120125859 | 11/2012 |
| KR | 10-2014-0031670 A | 3/2014 |
| KR | 10-2014-0046695 A | 4/2014 |

* cited by examiner

US 9,429,779 B2

ELECTRO-OPTIC MODULATOR INCLUDING COMPOSITE MATERIALS AND TESTING APPARATUS INCLUDING THE SAME

CROSS-REFERENCE TO RELATED APPLICATION

This application claims the benefit of Korean Patent Application No. 10-2014-0107764, filed on Aug. 19, 2014, in the Korean Intellectual Property Office, the disclosure of which is incorporated herein in its entirety by reference.

FIELD

The inventive concept relates to a display testing apparatus, and more particularly, to a testing apparatus including an electro-optic modulator.

BACKGROUND

Many flat panel displays (FPDs) such as liquid crystal displays (LCDs), field emission displays (FEDs), plasma display panels (PDPs), electroluminescences (ELs), light-emitting displays (LEDs), and organic LEDs (OLEDs) are commercially available. During a process of manufacturing a FPD, a thin-film transistor (TFT) array testing process may be performed. A TFT array is an aggregate of pixel electrodes of FPDs (e.g., LCDs) and switching devices configured to select the pixel electrodes. Various defects are likely to occur during the manufacturing process. The TFT array testing process may be broadly divided into a contact process of directly testing a TFT array for defects by using probe and a non-contact process of testing a TFT array for defects by using dislocation contrast or a voltage image method.

SUMMARY

Embodiments according to the inventive concept can provide an electro-optic modulator that can include a polymer film including liquid crystal (LC) droplets in the polymer film and a transparent electrode layer on an upper surface of the polymer film. A cholesteric liquid crystal (CLC) polymer reflection film can be on a lower surface of the polymer film opposite the transparent electrode layer.

In some embodiments according to the inventive concept, an electro-optic modulator can include a composite material layer including a polymer film and liquid crystal (LC) droplets distributed in the polymer film and a transparent electrode layer on a top surface of the composite material layer. A cholesteric liquid crystal (CLC) polymer reflection film can be on a bottom surface of the composite material layer.

In some embodiments according to the inventive concept, a testing apparatus can include a light source and an electro-optic modulator that includes a cholesteric liquid crystal (CLC) polymer reflection film disposed over a testing target object and wherein an intensity of reflected light from the electro-optic modulator varies with a voltage distribution of the testing target object. A beam splitter can be configured to transmit or reflect light and a first optical system can be configured to transfer light emitted by the light source to the beam splitter. A second optical system can be configured to transfer light output from the beam splitter to the electro-optic modulator and to transfer the reflected light for the electro-optic modulator to the beam splitter.

BRIEF DESCRIPTION OF THE DRAWINGS

Exemplary embodiments of the inventive concept will be more clearly understood from the following detailed description taken in conjunction with the accompanying drawings in which.

DETAILED DESCRIPTION OF THE EMBODIMENTS

Figure 1:
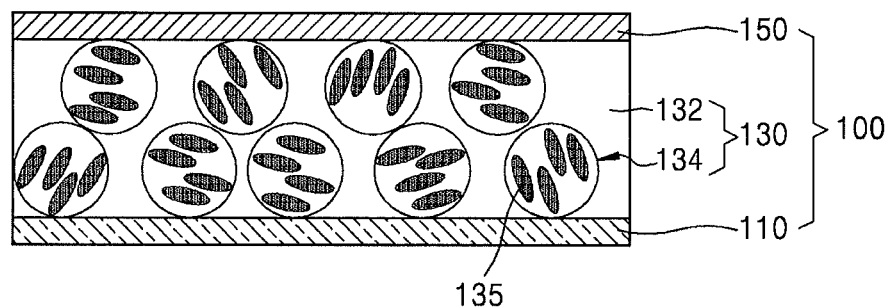
FIG. 1 is a cross-sectional view of an electro-optic modulator according to an exemplary embodiment.

As used herein, expressions such as "at least one of," when preceding a list of elements, modify the entire list of elements and do not modify the individual elements of the list.

The present inventive concept is described hereinafter with reference to the accompanying drawings, in which exemplary embodiments of the inventive concept are shown. This inventive concept may, however, be embodied in different forms and should not be construed as limited to the embodiments set forth herein. Rather, these embodiments are provided so that this disclosure is thorough and complete and fully conveys the scope of the inventive concept to one skilled in the art.

It will be understood that when an element or layer is referred to as being "on" or "connected to" another element or layer, it can be directly on or connected to the other element or layer or a third element or layer may be intervened. In the drawings, the thicknesses of layers and regions may be exaggerated for clarity. Descriptions of components and processing techniques that are irrelevant to the embodiments of the present inventive concept are omitted for brevity. Like reference numerals refer to like elements throughout. The terminology used herein to describe embodiments of the inventive concept is not intended to limit the scope of the inventive concept.

FIG. 1 is a cross-sectional view of an electro-optic modulator according to an exemplary embodiment.

Referring to FIG. 1, an electro-optic modulator 100 may include a reflection film 110, a composite material layer 130, and a transparent electrode layer 150.

The reflection film 110 may be formed of a cholesteric liquid crystal (CLC) polymer. The reflection film 110 may reflect light having a specific wavelength, from among incident light, and circularly polarize the incident light. Part of the circularly polarized light may be transmitted through the reflection film 110, and the remaining part of the circularly polarized light may be reflected by the reflection film 110. For example, the reflection film 110 may circularly polarize light having a specific wavelength, from among the incident light, transmit 50% of the circularly polarized light, and reflect 50% of the circularly polarized light.

The reflection film 110 may be formed by coating and curing the CLC polymer and have very excellent surface quality. For reference, a dielectric mirror film may be used instead of the reference film 110. The dielectric mirror film may include at least 10 layers formed by alternately depositing a high refractive index material and a low refractive index material on a substrate. However, as appreciated by the present inventors, since the dielectric mirror film is formed on a substrate, such as a polyethylene terephthalate (PET) substrate having a thickness of several μm, using a deposition process, such as a physical vapor deposition (PVD) process, minute cracks or protrusions may be formed, thereby degrading a surface quality of the dielectric mirror film. As further appreciated by the present inventors, due to these surface defects, the dielectric mirror film may be inadequate to detect defects in fine pixels (i.e., with a pitch of about 30 μm or less). Also, if the PET substrate is relatively thick, the electric field, which varies with a voltage distribution of a testing target object disposed under the PET substrate, may not be sufficiently transmitted to the composite material layer 130 disposed on the PET substrate.

However, the reflection film 110 applied to the electro-optic modulator 100 according to the present embodiment may be thinly formed of a CLC polymer. For example, the reflection film 110 may be formed of a CLC polymer to a thickness of about 3 μm or less. Thus, an electric field, which varies with a voltage distribution of a testing target object, may be relatively substantially transmitted to the composite material layer 130 disposed on the reflection film 110. Also, the reflection film 110 may be formed using coating and curing processes, which are used to form a polymer film. Thus, the surface quality (e.g., surface roughness and uniformity) of the reflection film 110 may be better than that of a dielectric mirror film. For example, in some embodiments, surface roughness and uniformity of the reflection film 110 formed of the CLC polymer may be at least five times as high as that of a dielectric mirror film. The reflection film 110 formed of the CLC polymer is described in further detail with reference to FIG. 3, for example.

The composite material layer 130 may include a polymer film 132 and LC droplets 134. For example, the composite material layer 130 may include polymer dispersed liquid crystals (PDLCs). Thus, the composite material layer 130 may have a structure in which a plurality of LC droplets 134 are dispersed in the polymer film 132. Each of the LC droplets 134 may contain a plurality of LC molecules 135.

More specifically, in some embodiments, the composite material layer 130 may include a PDLC film in which the LC droplets 134 having a size of several μm are dispersed in the polymer film 132 having a thickness of several tens of μm. When the PDLC film is interposed between two electrodes and an electric field is applied thereto, the LC molecules may be oriented toward the electric field. In this case, when an ordinary refractive index "$n_o$" of LCs becomes equal to a refractive index "$n_p$" of a polymer, the PDLC film may become transparent. When the electric field is removed, the directions of the LC molecules may become disordered due to surface anchoring energy, and an effective refractive index of the LCs may deviate from the refractive index "$n_p$" of the polymer. Thus, the PDLC film may become opaque due to scattering of light caused by a mismatch in the refractive indexes. Accordingly, since the PDLC film operates based on the scattering of light and does not need an additional polarizing plate, the optical efficiency may be increased.

A transparent electrode layer 150 may be formed of both a conductive material and a transparent material capable of transmitting light. For example, the transparent electrode layer 150 may be formed of indium tin oxide (ITO), antimony tin oxide (ATO), aluminum zinc oxide (AZO), indium zinc oxide (IZO), indium zinc tin oxide (IZTO), $SnO_2$, $In_2O_3$, or carbon nanotubes (CNTs). In the electro-optic modulator 100 according to the present embodiment, the transparent electrode layer 150 may be formed of ITO.

The electro-optic modulator 100 according to the present embodiment may include a CLC-polymer-based reflection film 110 having a relatively small thickness and a surface with excellent quality. Thus, the electro-optic modulator 100 may measure a voltage distribution of a testing target object disposed thereunder. For example, the electro-optic modulator 100 including the CLC-polymer-based reflection film 110 according to the present embodiment may be effectively used to detect pixel defects in a high-resolution display having a fine pitch less than or equal to 30 μm.

Figure 2A:
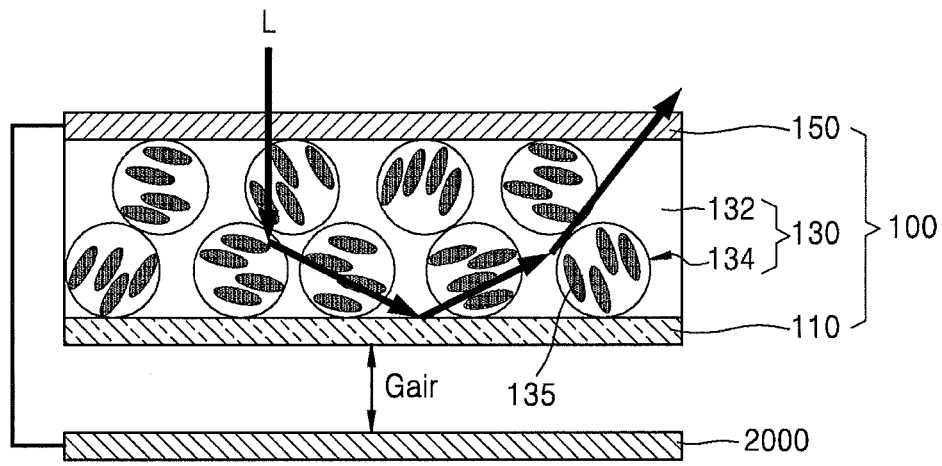
FIGS. 2A and 2B are cross-sectional views illustrating operations of the electro-optic modulator of FIG. 1.
Figure 2B:
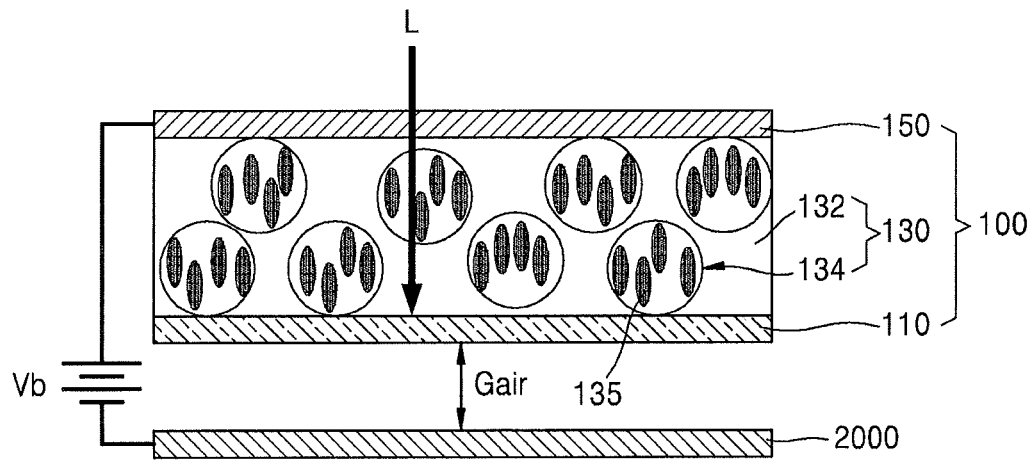

FIGS. 2A and 2B are cross-sectional views illustrating operations of the electro-optic modulator of FIG. 1. FIG. 2A illustrates a state when a bias voltage is not applied between the transparent electrode layer 150 and a testing target object 2000, and FIG. 2B illustrates a state when a bias voltage is applied between the transparent electrode layer 150 and a testing target object 2000.

Referring to FIG. 2A, the testing target object 2000 may be disposed under the electro-optic modulator 100. For example, the testing target object 2000 may be an FPD, such as a liquid crystal display (LCD) or an organic light emitting diode (OLED). The testing target object 2000 may include a thin-film transistor (TFT) array in which a plurality of pixel electrodes and a plurality of TFTs for driving the pixel electrodes are formed in a matrix shape.

As shown in FIG. 2A, a bias voltage may not be applied between the transparent electrode layer 150 and the testing target object 2000. Thus, LC molecules 135 may be disorderly arranged in the composite material layer 130. However, due to characteristics of LCs, the LC molecules 135 may not be completely disorderly arranged but be regularly arranged to some extent. For example, as shown in FIG. 2A, the LC molecules 135 contained in the LC droplets 134 may be arranged in about the same direction.

When the bias voltage is not applied, the LC molecules 135 in the composite material layer 130 may be disorderly arranged. Thus, incident light L may be scattered by the LC molecules 135 so that the composite material layer 130 may look opaque.

Referring to FIG. 2B, the testing target object 2000 may be disposed under the electro-optic modulator 100. A bias voltage Vb may be applied between the transparent electrode layer 150 and the testing target object 2000 as shown in FIG. 2B. With the application of the bias voltage Vb, LC molecules 135 contained in the LC droplets 134 may be aligned with an electric field generated by the bias voltage Vb. Accordingly, the bias voltage Vb may have a value sufficient to align all the LC molecules 135 of the LC droplets 134 in one direction. For example, in some embodiments, the bias voltage Vb may be several hundred volts.

An air gap Gair may be provided between the electro-optic modulator 100 and the testing target object 2000. For example, the air gap Gair between the electro-optic modulator 100 and the testing target object 2000 may have a width of about 50 μm. The air gap Gair may have a width such that a voltage distribution of the testing target object 2000 due to application of the bias voltage Vb and application of an operating voltage sufficiently affects the composite material layer 130. In other words, the air gap Gair may have a width such that an electric field generated according to the voltage distribution of the testing target object 2000 sufficiently affects the LC molecules 135 contained in the composite material layer 130. Although an air gap is shown in the figures, a gap with any medium that allows wireless coupling of the voltage on the testing target object 2000 to the composite layer may be used.

As shown in FIG. 2B, when the bias voltage Vb is applied, the LC molecules 135 contained in the composite material layer 130 may be aligned with an electric field of the bias voltage Vb. Thus, incident light L may pass through the aligned LC molecules 135 and reach the reflection film 110 to be reflected by the reflection film 110 so that the composite material layer 130 may look transparent. However, incident light L may not be wholly reflected due to circulation polarization and partial reflection characteristics of the reflection film 110.

For reference, a principle for detecting pixel defects of the testing target object 2000 by using the electro-optic modulator 100 will be briefly described. After a bias voltage Vb is applied between the transparent electrode layer 150 and the testing target object 2000, when an operating voltage is applied to the testing target object 2000, an electric field generated by each of the pixel electrodes may affect an arrangement state of the LC molecules 135 of the composite material layer 130. Here, an operating voltage may be, for example, about ±20 V, but is not limited thereto. When all pixels are normal, LC molecules 135 corresponding to each of the pixels may be uniformly arranged so that reflected light of incident light L may be uniform. However, when defective pixels are present, LC molecules corresponding to each of the defective pixels may be non-uniformly arranged so that reflected light of incident light L may be non-uniform. As a result, defects in pixels of the testing target object 2000 may be detected by analysing the uniformity of the reflected light.

Figure 3:
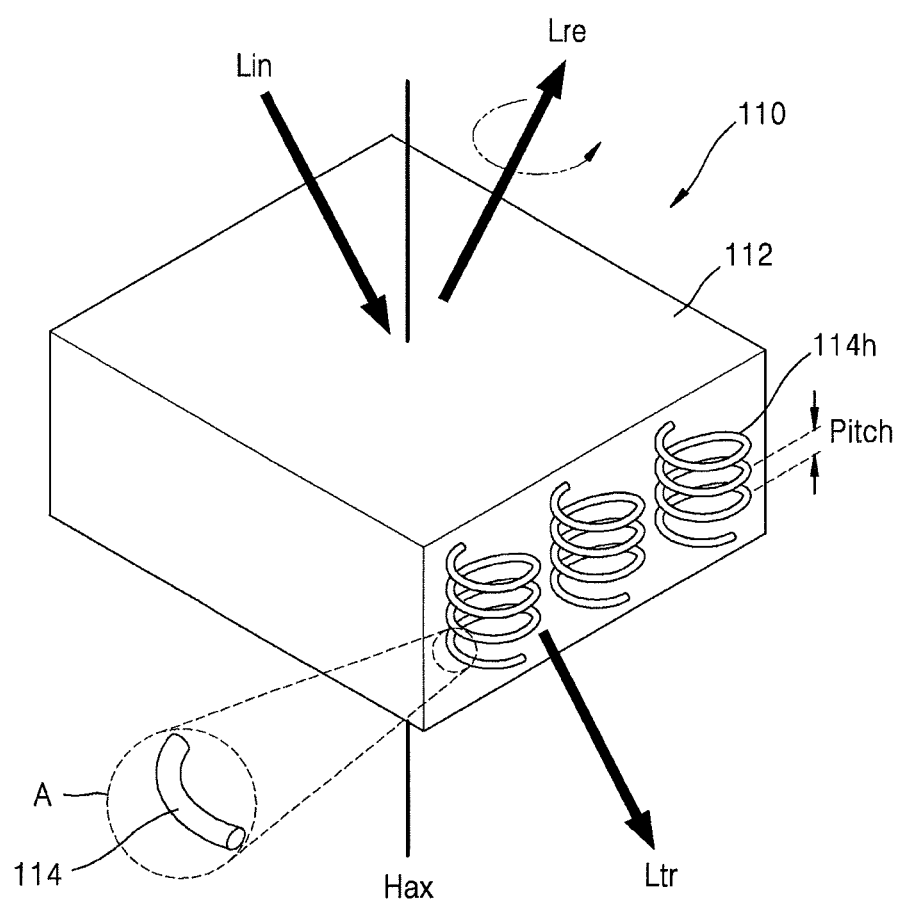
FIG. 3 is an enlarged perspective view of a reflection film for illustrating functions of the reflection film in the electro-optic modulator of FIG. 1.

FIG. 3 is an enlarged perspective view of a reflection film for illustrating functions of the reflection film in the electro-optic modulator of FIG. 1.

Referring to FIG. 3, the reflection film 110 may be a CLC polymer film. The CLC polymer film may include helix LCs 114h arranged in the polymer film 112. The CLC polymer film may reflect light having a particular wavelength by controlling a helix pitch. Accordingly, light that does not correspond to the particular wavelength may not be reflected but may be transmitted. Also, the CLC polymer film may circularly polarize unpolarized light, reflect 50% of polarized light, and transmit the remaining 50% of the polarized light.

In other words, unpolarized incident light Lin incident onto the CLC polymer film may be circularly polarized by the helix LCs 114h. Also, 50% of the polarized light may be reflected and output as reflected light Lre, and the remaining 50% of the polarized light may be transmitted and output as transmitted light Ltr. In addition, the reflected light Lre may be right-handed circularly polarized or left-handed circularly polarized in the direction of helices. A dashed circle A is an enlarged view of the LC molecule 114 contained in the helix LC 114h. Also, a solid line vertically passing through the CLC polymer film may refer to a helix rotation axis Hax of the helix LC 114h.

The reflection film 110 may be formed using coating and curing processes. Also, since the reflection film 110 according to the present embodiment is formed using coating and curing processes, the reflection film 110 may have better surface quality (e.g., surface roughness and uniformity) than a dielectric mirror film formed using a physical vapor deposition (PVD) process. Furthermore, since the reflection film 110 according to the present embodiment does not include an additional substrate, such as a PET substrate, the reflection film 110 may be relatively thin. For example, the reflection film 110 may be formed to a thickness of about 3 μm.

Figure 4:
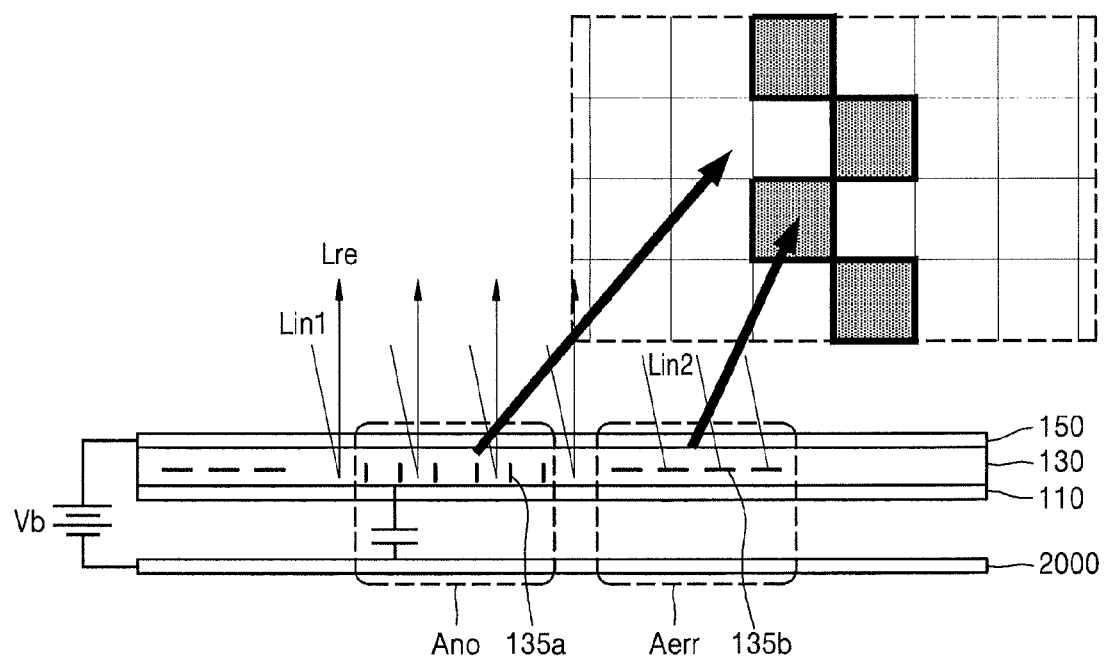
FIG. 4 is a diagram illustrating a detection of pixel defects in a flat-panel display (FPD) using the electro-optic modulator of FIG. 1.

FIG. 4 is a diagram illustrating detection of pixel defects of a flat-panel display (FPD) using the electro-optic modulator of FIG. 1.

Referring to FIG. 4, LC molecules 135a in a portion of the composite material layer 130 corresponding to a normal pixel Ano may be arranged in one direction due to a bias voltage Vb. Thus, incident light Lin1 may be reflected by the reflection film 110 and output as reflected light Lre. As indicated by a bold arrow, the portion of the composite material layer 130 corresponding to (i.e., opposite) the normal pixel Ano may be illustrated in a bright color due to reflected light Lre.

In contrast, LC molecules 135b of a portion of the composite material layer 130 corresponding to a defective pixel Aerr may not be arranged in one direction. Thus, incident light Lin2 may be scattered but not output as reflected light. Since the incident light Lin2 is not output as the reflected light, the portion of the composite material layer 130 corresponding to the defective pixel Aerr may be illustrated in a dark color as indicated by another bold arrow.

For reference, the diagram of FIG. 4 is simplified for clarity. That is, LC molecules 135b corresponding to the defective pixel Aerr may be arranged not in a horizontal direction but in an arbitrary direction. Also, since both a bias voltage and an operating voltage are applied during a process of testing a TFT array of an actual testing target object 2000, the LC molecules 135b corresponding to the defective pixel Aerr may also be aligned in the direction of an electric field due to a bias voltage and be affected by pixel defects. Thus, a direction in which the LC molecules 135b are actually arranged may slightly change. For example, although there is a difference in intensity between the portions of the composite material layer 130 corresponding to the defective pixel Aerr and the normal pixel Ano, reflected light may be output from the portion of the composite material layer 130 corresponding to the defective pixel Aerr.

Figure 5:
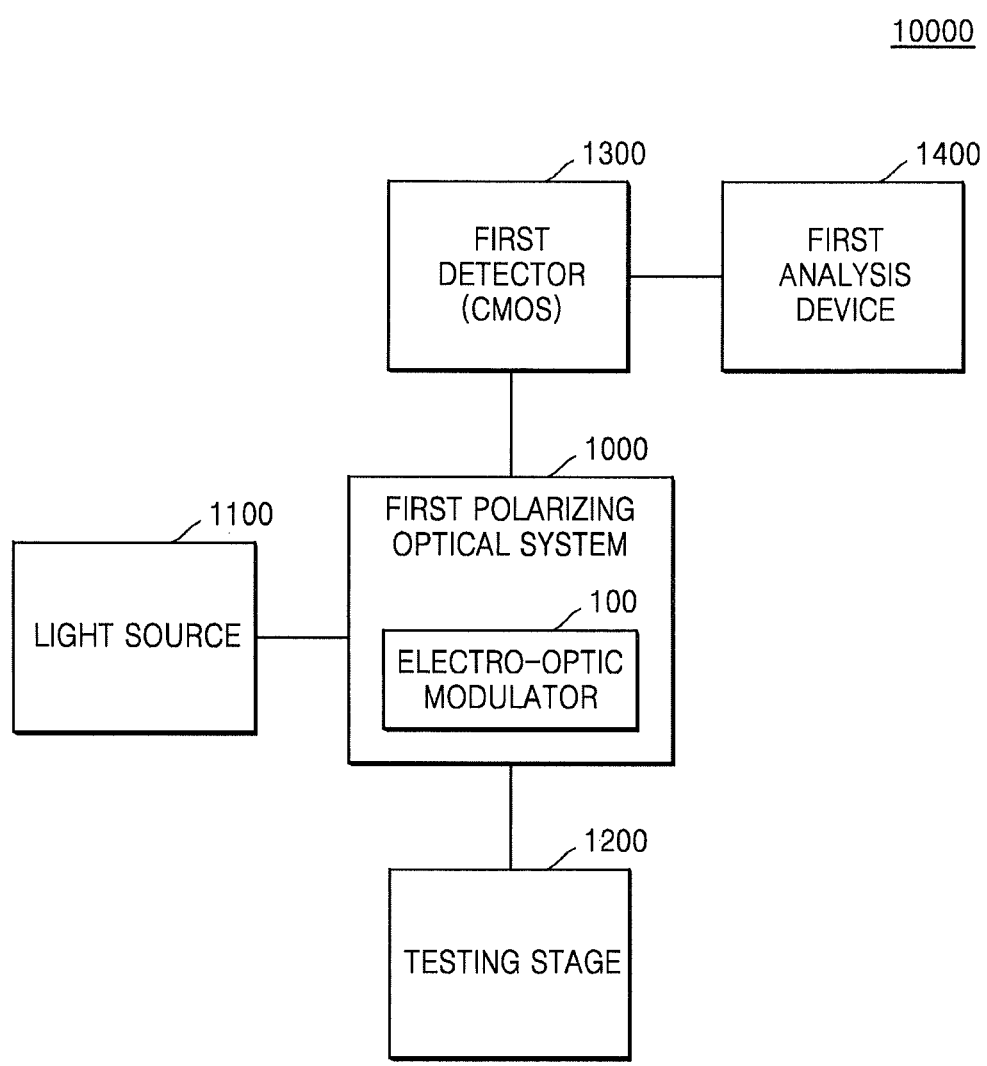
FIG. 5 is a block diagram of a testing apparatus including an electro-optic modulator according to an exemplary embodiment.

FIG. 5 is a block diagram of a testing apparatus including an electro-optic modulator according to an exemplary embodiment.

Referring to FIG. 5, a testing apparatus 10000 according to the present embodiment may include a first polarizing optical system 1000, a light source 1100, a testing stage 1200, a first detector 1300, and a first analysis device 1400.

The first polarizing optical system 1000 may include an electro-optic modulator 100. The electro-optic modulator 100 may be the electro-optic modulator 100 including the CLC-polymer-based reflection film 110 described with reference to FIG. 1. The first polarizing optical system 1000 may radiate light emitted by the light source 1100 to the electro-optic modulator 100, and transmit light reflected by the electro-optic modulator 100 to the first detector 1300.

Meanwhile, since the first polarizing optical system 1000 includes the electro-optic modulator 100, arrangement of a quarter wave plate may not be needed. For reference, the quarter wave plate may refer to an optical anisotropic double refraction plate which causes an optical path difference of a quarter wavelength between two polarization elements that oscillate in directions perpendicular to each other. When linearly polarized light is vertically incident onto the quarter wave plate such that an oscillation direction of light inside the quarter wave plate is at an angle of 45° with an oscillation direction of incident light, transmitted light may be circularly polarized.

As described above, the electro-optic modulator 100 of FIG. 1 may include a CLC-polymer-based reflection film 110 capable of circularly polarizing incident light. Thus, the first polarizing optical system 1000 may not need to include an additional quarter wave plate.

The light source 1100 may be an apparatus capable of generating light that may be incident to the first polarizing optical system 1000. Light generated by the light source 1100 may be unpolarized light. The unpolarized light may be polarized by a polarizer included in the first polarizing optical system 1000, and incident to the electro-optic modulator 100. Also, reflected light output by the electro-optic modulator 100 may also be polarized by a polarizer and transmitted to the first detector 1300.

The testing stage 1200, which is an apparatus on which the testing target object (refer to 2000 in FIG. 2A) is disposed, may move in at least one of an x direction, a y direction, and a z direction. The testing target object 2000 disposed on the testing stage 1200 may be, for example, an FPD including a TFT array.

The first detector 1300 may be an apparatus that receives reflected light output by the first polarizing optical system 1000. The first detector 1300 may be, for example, a complementary-metal-oxide semiconductor (CMOS) camera. Since the CMOS camera is commonly capable of capturing images at high speed, the TFT array of the testing target object 2000 may be tested at low cost and with high speed. However, the CMOS camera may have a signal-to-noise ratio (SNR) of about 43 dB, which is less than that of a charge-coupled device (CCD) camera. Accordingly, several images may be overlapped and averaged to increase the SNR of the CMOS camera when the testing apparatus 10000, according to the present embodiment, is employed. For example, the first analysis device 1400 may further include an image grabber and overlap and average images so as to provide SNRs at a desired level. In some cases, the image grabber may be included in the first detector 1300.

The first analysis device 1400 may remove non-uniform elements from an image received from the first detector 1300 using a predetermined algorithm and remove defects in pixels. As described above, the first analysis device 1400 may include an image grabber to provide high SNR. For reference, when a high-speed CMOS camera is used, it may be difficult to receive output data at a normal speed due to the limit of an input bandwidth of a personal computer (PC). Thus, the testing apparatus 10000 according to the present embodiment may cumulatively average a desired number of images using the image grabber, use the average image as an analysis image, to provide adequate bandwidth. For example, when 8 43 dB images obtained by a CMOS camera are cumulatively averaged, an image having SNR of about 50 dB may be obtained.

Meanwhile, errors due to non-uniformity may be present in images obtained by the first detector 1300. The first analysis device 1400 may use defect detecting algorithms to remove the non-uniform elements from the images. For example, the defect detecting algorithms may include at least one of a method of using a calibration image and a method of using a local threshold value. A defect detecting algorithm may be performed by a computer, such as a PC. Accordingly, the first analysis device 1400 may be included and embodied in the computer.

Since the testing apparatus 10000 according to the present embodiment includes the electro-optic modulator 100 described with reference to FIG. 1, defects in pixels having a fine pitch may be detected. Also, since the quarter wave plate is not required, the first polarizing optical system 1000 may be simply configured. The testing apparatus 10000 according to the present embodiment may perform a testing process at low cost and at high speed by using the CMOS camera as the first detector 1300. Also, since the testing apparatus 10000 according to the present embodiment includes the first analysis device 1400 that includes the image grabber and uses the defect detecting algorithm, a high SNR may be obtained, and non-uniform elements may be removed from images. As a result, the testing apparatus 10000 according to the present embodiment may easily and precisely and with high speed detect pixel defects in a high-resolution display device having a fine pitch of about 30 µm or less.

Figure 6:
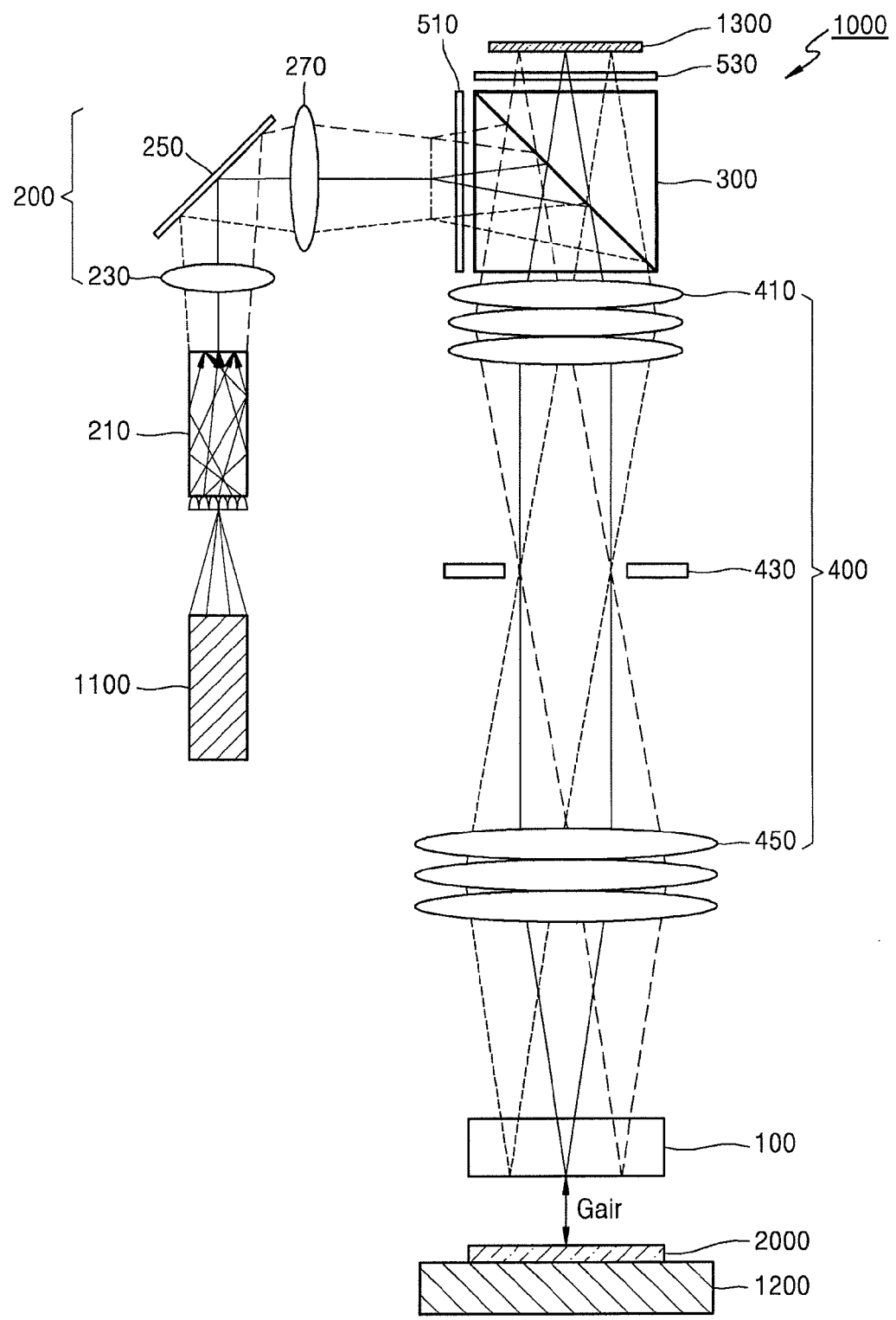
FIG. 6 is a schematic illustration of a polarization optical system of the testing apparatus of FIG. 5.

FIG. 6 is a schematic illustration of a polarization optical system of the testing apparatus of FIG. 5.

Referring to FIG. 6, a first polarizing optical system 1000 according to the present embodiment may include an electro-optic modulator 100, a first optical system 200, a beam splitter 300, a second optical system 400, and first and second polarizers 510 and 530.

The electro-optic modulator 100 may be, for example, the electro-optic modulator described above with reference to FIGS. 1 through 3.

The first optical system 200 may transfer light emitted by a light source 1100 to the beam splitter 300. The first optical system 200 may include a rod pipe 210, a beam expander 230, a relay, a collimation lens or condensing lens 270, and a mirror 250.

The beam splitter 300 may reflect light (which is transferred from the light source 1100 through first optical system 200) and transfer the reflected light to the second optical system 400. Also, the beam splitter 300 may transmit light (which is reflected by the electro-optic modulator 100 and transferred through the second optical system 400) and transfer the transmitted light to the first detector 1300. In some cases, the beam splitter 300 may transmit light emitted by the light source 1100 and transfer the transmitted light to the electro-optic modulator 100, and reflect light which is reflected by the electro-optic modulator 100 and transfer the reflected light to the first detector 1300.

The second optical system 400 may transfer light which is reflected by the beam splitter 300 to the electro-optic modulator 100, and transfer light which is reflected by the electro-optic modulator 100 to the beam splitter 300. The second optical system 400 may include a tube lens 410, a double telecentric optical system 430, and an objective lens 450. Light incident onto the electro-optic modulator 100 may be P-polarized light polarized by the first polarizer 510, and light reflected by the electro-optic modulator 100 may be light circularly polarized by the reflection film 110.

The first polarizer 510 may be disposed in front of an incidence surface of the beam splitter 300 onto which light emitted by the light source 1100 is incident. That is, the first polarizer 510 may be disposed between the first optical system 200 and the beam splitter 300. The first polarizer 510 may allow only one of a transverse magnetic (TM) wave and a transverse electric (TE) wave to pass therethrough. In other words, the first polarizer 510 may P-polarize incident light to generate a TM wave (or P wave) or S-polarize incident light to generate a TE wave (or S wave).

The second polarizer 530 may be disposed in front of an emission surface of the beam splitter 300 from which light which is reflected by the electro-optic modulator 100 and transmitted through the beam splitter 300 is output. The second polarizer 530 may serve the opposite function to that of the first polarizer 510. For example, when the first polarizer 510 transmits a TM wave, the second polarizer 530 may transmit a TE wave. When the first polarizer 510 transmits a TE wave, the second polarizer 530 may transmit a TM wave. In other words, when the first polarizer 510 P-polarizes incident light, the second polarizer 530 may S-polarize incident light. Conversely, when the first polarizer 510 S-polarizes incident light, the second polarizer 530 may P-polarize incident light.

Assuming that the first polarizer 510 and the second polarizer 530 are disposed in the front of the incidence surface and the emission surface of the beam splitter 300 and a polarization phenomenon does not occur in the electro-optic modulator 100, while unpolarized light emitted by the light source 1100 passes through the first polarizer 510, the unpolarized light may be P-polarized, only a TM wave may be incident onto the electro-optic modulator 100, reflected, transmitted through the beam splitter 300, and incident onto the second polarizer 530. However, since the second polarizer 530 transmits only the TE wave, any light cannot be finally output from the second polarizer 530. However, circular polarization actually occurs in the electro-optic modulator 100, and part of light reflected by the electro-optic modulator 100 may be transmitted through the second polarizer 530 and output.

The first polarizer 510 and the second polarizer 530 may be prepared to remove light noise as much as possible. In general, the light noise may be minimized while passing through the first and second polarizer 510 and 530.

As described above, since the first polarizing optical system 1000 according to the present embodiment includes the electro-optic modulator 100 including the CLC-polymer-based reflection film 110, defects in pixels having a fine pitch may be detected. Also, an additional quarter wave plate may not be needed due to circular polarization characteristics of the reflection film 110.

Figure 7A:
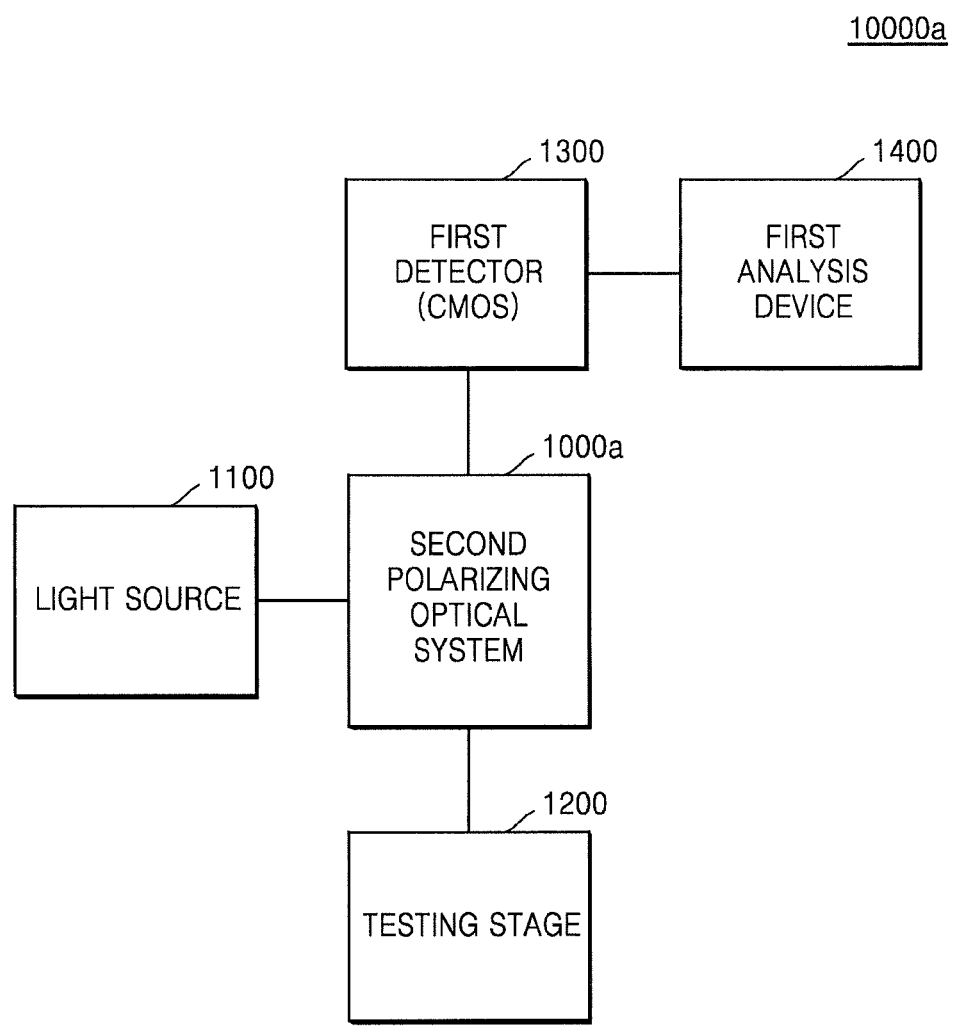
FIGS. 7A and 7B are block diagrams of a testing apparatus according to an exemplary embodiment.
Figure 7B:
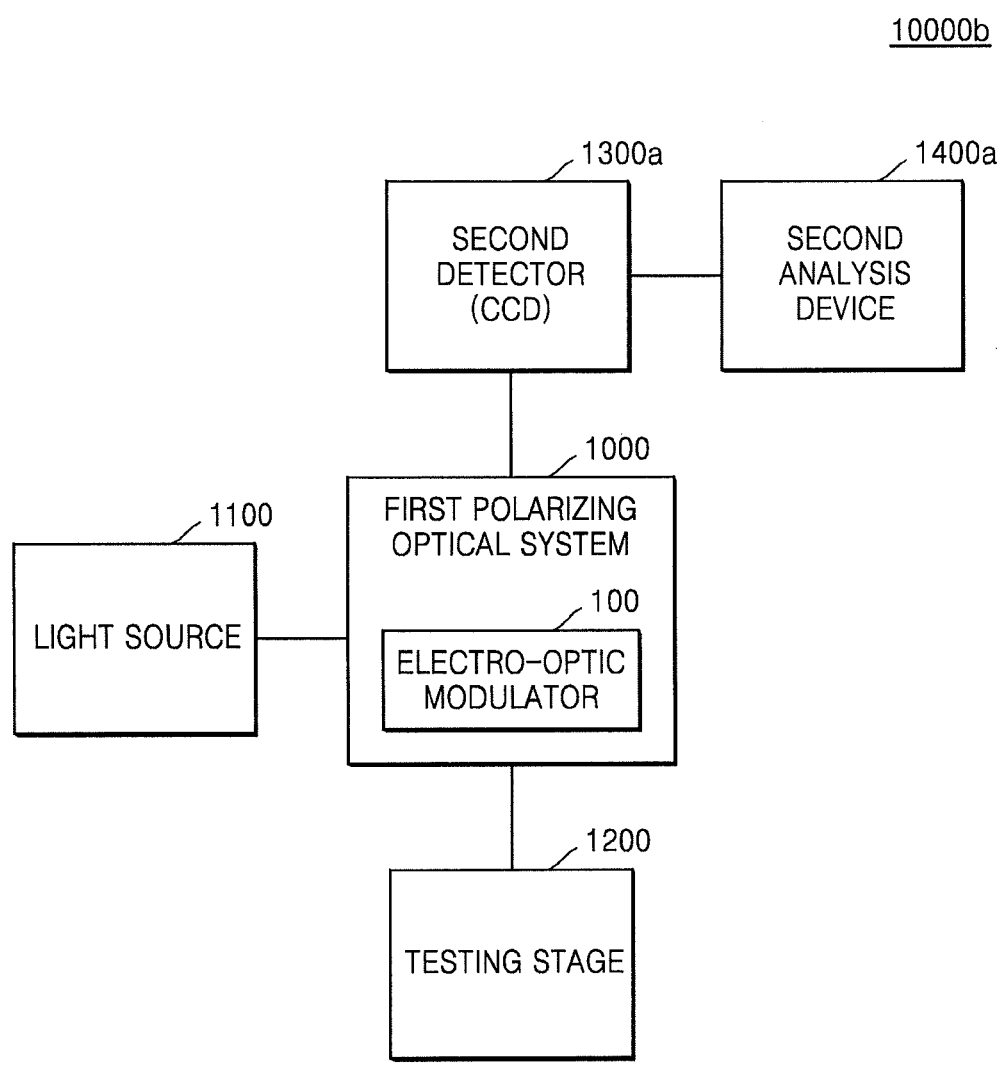

FIGS. 7A and 7B are block diagrams of a testing apparatus according to an exemplary embodiment.

Referring to FIG. 7A, a testing apparatus 10000a according to the present embodiment may be similar to the testing apparatus 10000 of FIG. 5 except that the testing apparatus 10000a includes a second polarizing optical system 1000a. Specifically, the second polarizing optical system 1000a may include an electro-optic modulator, which may include a dielectric mirror film instead of a CLC-based reflection film. Also, the second polarizing optical system 1000a may further include a quarter wave plate that circularly polarizes incident light.

Meanwhile, like the testing apparatus of FIG. 5, the testing apparatus 10000a according to the present embodiment may include a CMOS camera as the first detector 1300 so that defects in pixels may be tested. Also, the testing apparatus 10000a according to the present embodiment may include a first analysis device 1400 that includes an image grabber and utilizes a defect detecting algorithm. Thus, an SNR may be increased, and defect detection performance may be improved by largely removing image non-uniformity.

Referring to FIG. 7B, a testing apparatus 10000b according to the present embodiment may be similar to the testing apparatus 10000 of FIG. 5 except that the testing apparatus 10000b includes a second detector 1300a and a second analysis device 1400a. Specifically, like the testing apparatus 10000 of FIG. 5, the testing apparatus 10000b according to the present embodiment may include a first polarizing optical system 1000 including a CLC-polymer-based reflection film 110. Thus, defects in pixels having a fine pitch may be detected. Also, since a quarter wave plate is not needed, the first polarizing optical system 1000 may be simply configured.

However, in the testing apparatus 10000b according to the present embodiment, the second detector 1300a may be embodied as a CCD camera instead of the CMOS camera. An image of the CCD camera may have a relatively high SNR. However, when necessary, a pixel size of the CCD camera may be increased to increase a full-well capacity of a pixel. For example, the full-well capacity of the CCD camera may be set to 120,000 electrons (e−) or more so that an image having an SNR of 50 dB or more may be embodied. Thus, defects in pixels having a fine pitch may be detected.

The second analysis device 1400a may or may not include the image grabber. For example, when an image of the CCD camera has a high SNR, the second analysis device 1400a may not include an image grabber. In contrast, when an SNR of an image of the CCD camera is low and needs to be increased, the second analysis device 1400a may include the image grabber.

The second analysis device 1400a may extract a defect image by applying a global threshold value. However, application of a local threshold value is not necessarily excluded. In some cases, a defect detecting algorithm for generating a corrected voltage image using a calibration image may be employed.

The testing apparatus 10000b according to the present embodiment may include a first polarizing optical system 1000. The second detector 1300a and the second analysis device 1400a may be replaced by other components as needed. For example, the second detector 1300a may be replaced by the first detector 1300 of the testing apparatus 10000 of FIG. 5. Also, the second analysis device 1400a may be replaced by the first analysis device 1400. Furthermore, the second analysis device 1400a may use at least one of an image grabber, a defect detecting algorithm using a calibration image, and a local threshold value to extract a defect image as needed.

Figure 8A:
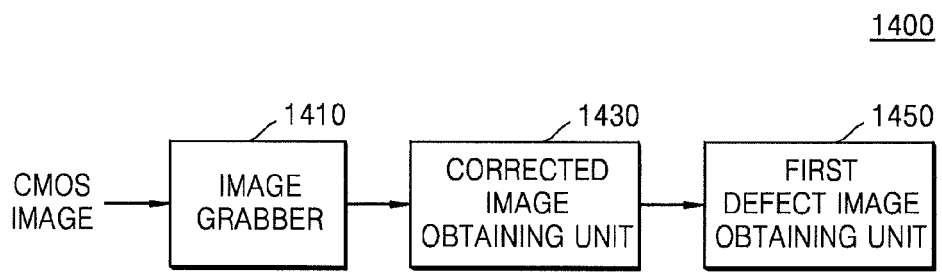
FIG. 8A through 8C are detailed block diagrams of an analysis apparatus included in a testing apparatus according to an exemplary embodiment.
Figure 8B:
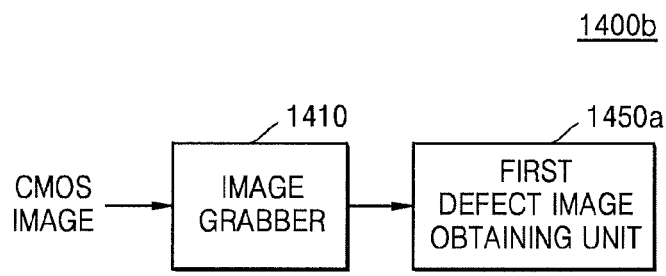
Figure 8C:
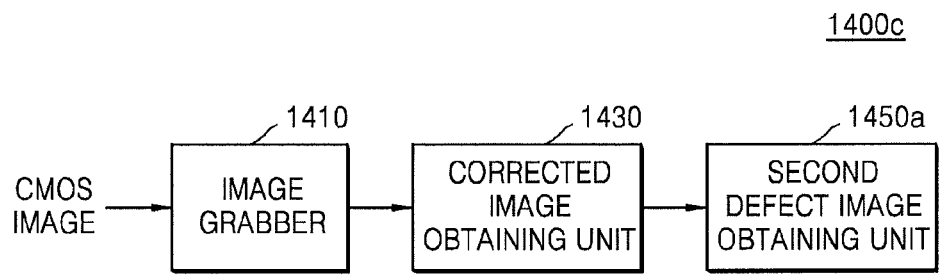

FIG. 8A through 8C are block diagrams of an analysis apparatus included in a testing apparatus according to an exemplary embodiment.

Referring to FIG. 8A, a first analysis device 1400 according to the present embodiment may include an image grabber 1410, a corrected image obtaining unit 1430, and a first defect image obtaining unit 1450. As described above, the image grabber 1410 may accumulate and average a plurality of images obtained by a CMOS camera and form an image having a high SNR. For example, the image grabber 1410 may accumulate and average 8 images obtained by the CMOS camera and thus form a high-resolution image having an SNR of 50 dB.

In general, the defect detecting algorithm may be based on a principle that after a calibration image is generated based on the influence of the non-uniform elements, errors caused by the non-uniform elements are removed from the operating voltage image. The corrected image obtaining unit 1430 may minimize image non-uniformity caused by the non-uniform elements by using the defect detecting algorithm, and obtain a corrected voltage image.

The corrected image obtaining unit 1430 may remove a non-uniform element from an image captured by the image grabber 1410. That is, due to non-uniformity characteristic of the testing apparatus, the image obtained by the first detector 1300 and the image grabber 1410 may have an error.

More specifically, differences in electro-optic modulation characteristics may occur among respective regions of an electro-optic modulator having a size of about 7 inches or more. The differences in electro-optic modulation characteristics may be typically affected by non-uniformity in thickness of an LC layer (i.e., a composite material layer). Also, not only non-uniformity in air gap between an electro-optic modulator and a testing target object, but also non-uniformity caused by a fine height difference between protrusions of ceramic chucks configured to support the testing target object may lead to the differences in the electro-optic modulation characteristics. Due to the above-described non-uniform elements, even if an electric field is applied at a uniform intensity to the electro-optic modulator, reflected light may be incident at non-uniform intensity onto the first detector 1300 in respective regions.

The corrected image obtaining unit 1430 may utilize a defect detecting algorithm to remove non-uniform elements from the image. More specifically, to remove the non-uniform elements from the image, an additional calibration image for removing the non-uniform elements may be obtained and utilized each time an image is captured. That is, first, while pixel electrodes of the testing target object are not being driven, only a bias voltage may be applied to an electro-optic modulator to obtain a calibration image. An appropriate voltage may be applied to the pixel electrode with application of the bias voltage, thereby obtaining a voltage image of the pixel electrodes, that is, an operating voltage image. Thereafter, brightnesses of the operating voltage image may be respectively divided by brightnesses of the calibration image, thereby obtaining a corrected voltage image of which brightness is formed in proportion to a voltage of an actual pixel electrode. Here, the bias voltage may be several hundred volts, and the operating voltage may be about ±several tens of volts.

The first defect image obtaining unit 1450 may extract a defect image, which explicitly indicates an actually defective portion, from the corrected voltage image obtained by the corrected image obtaining unit 1430.

For reference, extraction of a defect image may include applying a global threshold value to each of pixels and indicating a pixel having a lower value than the global threshold value as a defective pixel. However, it may be undesirable to equally apply the global threshold value to all regions of a large-area testing target object because non-uniform elements may be still present in respective regions, and a defect image obtained by applying the global threshold value may still contain errors due to the non-uniform elements.

The first defect image obtaining unit 1450 may apply a local threshold voltage instead of the global threshold value and extract a defect image. Specifically, an entire region of a testing target object may be divided into a plurality of small regions, local threshold values corresponding to the respective small regions may be determined, and the local threshold values may be applied to the respective small regions to extract the defect image. For example, each of the local threshold values may be calculated using the average and standard deviations of voltages of pixels of the corresponding small region. Meanwhile, the small regions may have one of various sizes. For example, when the testing target object includes 5000×5000 pixels, the testing target object may be divided into small regions having a size of 10×10 pixels. Thus, when each of the small regions has a size of 10×10 pixels, the testing target object may be divided into about 250000 small regions. However, a local threshold value may be calculated and a local threshold value applied to the corresponding small region at high speed by using a parallel computing method.

As described above, the first defect image obtaining unit 1450 according to the present embodiment may apply a local threshold value to each of the small regions instead of applying a global threshold value to the corrected voltage image obtained using the corrected image obtaining unit 1430, so that the influence of the remaining non-uniformity elements, which are not yet removed, may be removed again to calculate a final defect image. Meanwhile, a pixel mapping process may be performed on the corrected voltage image so that the corrected voltage image may be converted into a voltage map image. Thus, the defect image may be obtained by applying the local threshold voltage to the voltage map image.

Referring to FIG. 8B, unlike the first analysis device 1400 of FIG. 8A, a first analysis device 1400b according to the present embodiment may not include a corrected image obtaining unit 1430. That is, when a non-uniform element of the testing apparatus is not large, application of a defect detecting algorithm using the corrected image obtaining unit 1430 may be omitted. Also, the first defect image obtaining unit 1450a may remove non-uniform elements from each of the small regions by applying a local threshold value to the corresponding small region.

Referring to FIG. 8C, unlike the first analysis device 1400 of FIG. 8A, a first analysis device 1400c according to the present embodiment may include a second defect image obtaining unit 1450a. Unlike the first defect image obtaining unit 1450 of FIG. 8A, the second defect image obtaining unit 1450a may apply a global threshold value. For example, when non-uniform elements remaining in a corrected voltage image obtained by the corrected image obtaining unit 1430 are not large, the second defect image obtaining unit 1450a may apply the global threshold value, and calculate a defect image at high speed.

Figure 9:
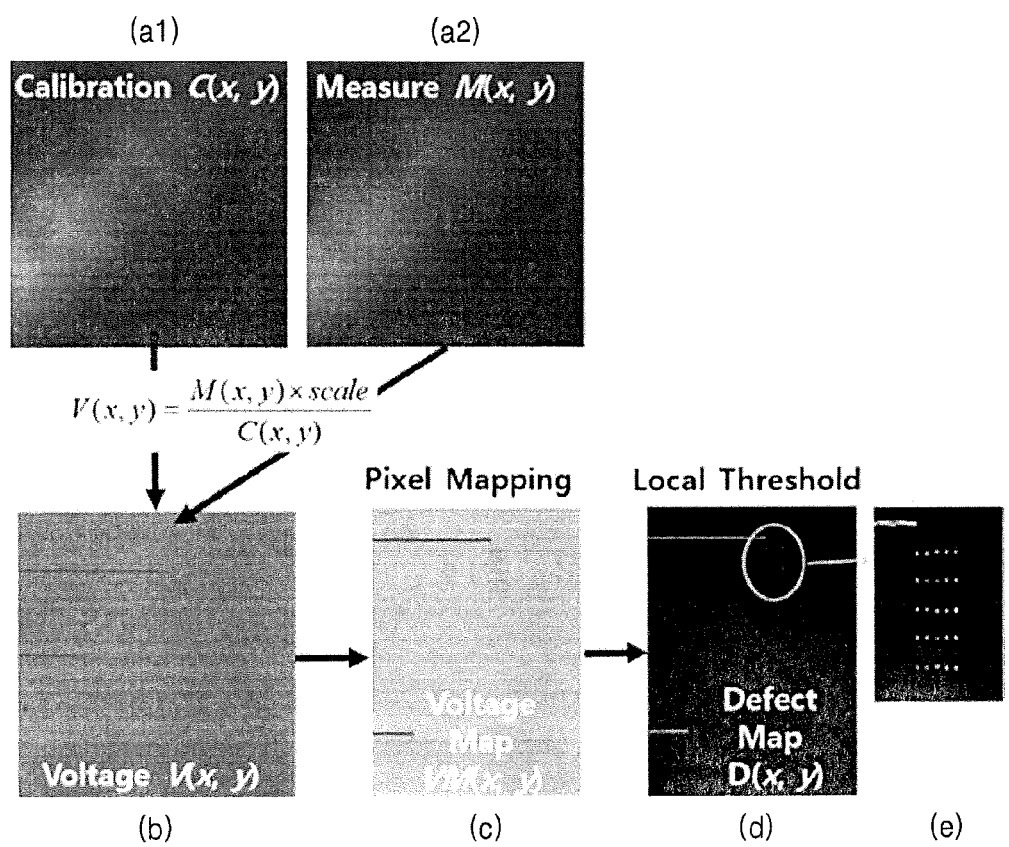
FIG. 9 are images illustrating a process of detecting pixel defects in a display by using the testing apparatus of FIG. 5.

FIG. 9 are images illustrating a process of detecting pixel defects in a display using the testing apparatus of FIG. 5, with reference to FIGS. 1 through 8C.

Referring to FIG. 9, first, a bias voltage may be applied between the electro-optic modulator 100 and the testing target object 2000 to obtain a calibration image "a1". Thereafter, an appropriate voltage may be applied to pixel electrode with application of the bias voltage, thereby obtaining an operating voltage image "a2". Thereafter, brightnesses of respective pixels of the operating voltage image "a2" may be divided by brightnesses of respective pixels of the calibration image "a1," thereby obtaining a corrected voltage image "b". Meanwhile, as denoted by a numerical expression in FIG. 9, when the corrected voltage image "b" is obtained, a scaling factor may be used. The scale factor may be a factor that allows a voltage of each of the pixels of the corrected voltage image "b" to become equal to or correspond to a value of an actual pixel. For example, when the bias voltage is about 300V and the operating voltage is about 20V, a corrected voltage image can be calculated by a division, 320/300≈1.07. Thus, a difference may occur between the value of 1.07 and an actual operating voltage of 20V. Accordingly, the scale factor may be added to correct the difference.

After obtaining the corrected voltage image "b", a voltage map image "c" may be generated using a pixel mapping process. The corrected voltage image "b" may be an image based on pixels of a camera having a very small size. Accordingly, the corrected voltage image "b" may be different from an image based on large-sized pixels of testing target object (e.g., LCD). To control a mismatch between the images, a process of mapping the pixels of the camera to the pixels of the LCD may be performed. For example, several to several tens of pixels of the camera may be mapped to one pixel of the LCD.

After the voltage map image "c" is obtained, a defect image "d" may be calculated and obtained by applying a local threshold value. That is, the local threshold value may be applied to each of small regions, and regions having less than the local threshold value may be indicated as defective portions. In the defect image "d", the defective portion is indicated in a white color. The defective portion may indicate a line defect, a point defect, or a plane defect. The point defect may be more clearly observed from a right enlarged view "e".

While the inventive concept has been particularly shown and described with reference to exemplary embodiments thereof, it will be understood that various changes in form and details may be made therein without departing from the spirit and scope of the following claims.

What is claimed:

1. An electro-optic modulator comprising:
    a composite material layer including a polymer film and liquid crystal (LC) droplets distributed in the polymer film;
    a transparent electrode layer on a top surface of the composite material layer; and
    a cholesteric liquid crystal (CLC) polymer reflection film on a bottom surface of the composite material layer, wherein the CLC polymer reflection film has a thickness of about 3 microns to about several microns.

2. The electro-optic modulator of claim 1, wherein each of the LC droplets includes a plurality of LC molecules, wherein LCs contained in the reflection film have a helix structure, with a helix pitch, configured to provide circularly polarized reflected light according to handedness of the helix structure.

3. The electro-optic modulator of claim 2, wherein the LC molecules are aligned due to a bias voltage applied between a testing target object disposed under the reflection film and the transparent electrode layer,
    light passes through the transparent electrode layer toward the reflection film, and
    an aligned state of the LC molecules corresponding to the testing target object varies with a voltage distribution of the testing target object, and an intensity of the circularly polarized reflected light varies with the aligned state of the LC molecules.

4. A testing apparatus comprising:
    a light source;
    an electro-optic modulator including a cholesteric liquid crystal (CLC) polymer reflection film disposed over a testing target object, wherein an intensity of reflected light from the electro-optic modulator varies with a voltage distribution of the testing target object;
    a beam splitter configured to transmit or reflect light;
    a first optical system configured to transfer light emitted by the light source to the beam splitter; and
    a second optical system configured to transfer light output from the beam splitter to the electro-optic modulator and transfer the reflected light for the electro-optic modulator to the beam splitter, wherein the electro-optic modulator comprises:
    a composite material layer on the reflection film and including a polymer film and a plurality of liquid crystal (LC) droplets; and
    a transparent electrode layer on a top surface of the composite material layer,
    wherein an aligned state of LC molecules in the droplets varies with a bias voltage applied between the transparent electrode layer and the testing target object and the voltage distribution of the testing target object.

5. The testing apparatus of claim 4, wherein the testing apparatus comprises:
    a testing stage on which the testing target object is disposed; and
    a detector configured to receive the reflected light transmitted through the beam splitter.

6. The testing apparatus of claim 5, wherein a first polarizer is between the first optical system and the beam splitter and allows a transverse magnetic (TM) wave or a transverse electric (TE) wave to pass therethrough, and
    wherein a second polarizer is between the beam splitter and the detector and allows the TM wave or the TE wave to pass therethrough.

7. The testing apparatus of claim 5, wherein the detector is a complementary-metal-oxide semiconductor (CMOS) camera or a charge-coupled device (CCD) camera.

8. The testing apparatus of claim 5, wherein the detector is a CMOS camera, the testing apparatus further comprises:
    an image grabber that accumulates and averages a plurality of images obtained by the CMOS camera and generates an average image.

9. The testing apparatus of claim 8, wherein the images obtained by the CMOS camera have a signal-to-noise ratio (SNR) of about 43 dB, and
    the average image generated from the image grabber has an SNR of about 50 dB or higher.

10. The testing apparatus of claim 4, wherein:
    when the testing target object is tested, a bias voltage is applied between the testing target object and the transparent electrode layer, and an operating voltage is applied to the testing target object.

11. The testing apparatus of claim 10, wherein a calibration image is obtained by applying the bias voltage without applying the operating voltage,
    an operating voltage image is obtained by applying the bias voltage and the operating voltage, and
    a corrected voltage image is obtained by dividing the operating voltage image by the calibration image.

12. The testing apparatus of claim 11, wherein after the corrected voltage image is converted into a voltage map image by using a pixel mapping process, the voltage map image is divided into a plurality of small regions, and non-uniform elements are removed by applying a local threshold value to each of the small regions of the voltage map image to obtain a defect image.

13. An electro-optic modulator comprising:
    a polymer film including liquid crystal (LC) droplets in the polymer film;
    a transparent electrode layer on an upper surface of the polymer film; and a cholesteric liquid crystal (CLC) polymer reflection film on a lower surface of the polymer film opposite the transparent electrode layer wherein the CLC polymer reflection film is configured for wireless electrical coupling to a target testing object that is spaced apart from the CLC polymer reflection film by a gap.

14. The electro-optic modulator of claim 13 wherein each of the LC droplets includes a plurality of LC molecules that are configured for orientation responsive to the wireless electrical coupling.

15. The electro-optic modulator of claim 14 wherein the gap is about 50 microns and the wireless electrical coupling results from a bias voltage applied to the target testing object.

16. The electro-optic modulator of claim 15 wherein the CLC polymer reflection film has a thickness of about 3 microns to about several microns.

17. The electro-optic modulator of claim 14 wherein the LC molecules are in a helix shape having an associated handedness.

18. The electro-optic modulator of claim 13 further comprising:
a target testing object that is spaced apart from the CLC polymer reflection film by a gap.

* * * * *